(12) United States Patent
Thienphrapa et al.

(10) Patent No.: US 12,257,104 B2
(45) Date of Patent: Mar. 25, 2025

(54) HYBRID ROBOTIC-IMAGE PLANE CONTROL OF A TEE PROBE

(71) Applicant: KONINKLIJKE PHILIPS N.V., Eindhoven (NL)

(72) Inventors: Paul Thienphrapa, Cambridge, MA (US); Sean Joseph Kyne, Brookline, MA (US); Molly Lara Flexman, Melrose, MA (US); Ameet Kumar Jain, Boston, MA (US); Sibo Li, Waltham, MA (US); Kunal Vaidya, Boston, MA (US); Marcin Arkadiusz Balicki, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 340 days.

(21) Appl. No.: 17/783,387

(22) PCT Filed: Dec. 8, 2020

(86) PCT No.: PCT/EP2020/084971
§ 371 (c)(1),
(2) Date: Jun. 8, 2022

(87) PCT Pub. No.: WO2021/116051
PCT Pub. Date: Jun. 17, 2021

(65) Prior Publication Data
US 2023/0012353 A1    Jan. 12, 2023

Related U.S. Application Data

(60) Provisional application No. 62/947,153, filed on Dec. 12, 2019.

(51) Int. Cl.
*A61B 8/00* (2006.01)
*A61B 8/08* (2006.01)
*A61B 1/00* (2006.01)

(52) U.S. Cl.
CPC .......... *A61B 8/4245* (2013.01); *A61B 8/0883* (2013.01); *A61B 1/0005* (2013.01)

(58) Field of Classification Search
CPC ................ A61B 2090/378; A61B 8/58; A61B 2017/00106; A61B 8/0883; A61B 8/4245
See application file for complete search history.

(56) References Cited

U.S. PATENT DOCUMENTS 5,050,610 A    9/1991  Oaks
11,185,308 B2  11/2021 Yasuhiko
(Continued)

FOREIGN PATENT DOCUMENTS

| EP | 2158846 A2    | 3/2010 |
|----|---------------|--------|
| JP | 2019-093123 A | 6/2019 |
| WO | 2019/175129 A1| 9/2019 |

OTHER PUBLICATIONS

International Search Report and Written Opinion Dated Mar. 5, 2021 for International Application No. PCT/EP2020/084971 Filed Dec. 8, 2020.

*Primary Examiner* — Gerald Johnson (57) ABSTRACT

The following relates generally to systems and methods of transesophageal echocardiography (TEE) automation. Some aspects relate to a TEE probe with ultrasonic transducers on a distal end of the TEE probe. In some implementations, if a target is in a field of view (FOV) of the ultrasonic transducers, an electronic beam steering of the probe is adjusted; if the target is at an edge of the FOV, both the electronic beam steering and mechanical joints of the probe are adjusted; and if the target is not in the FOV, only the mechanical joints of the probe are adjusted.

20 Claims, 7 Drawing Sheets

(56) References Cited

U.S. PATENT DOCUMENTS

| | | | |
|---|---|---|---|
| 2017/0007202 A1* | 1/2017 | Peszynski | A61B 8/54 |
| 2017/0105685 A1 | 4/2017 | Schafer | |
| 2018/0085090 A1* | 3/2018 | Park | A61B 8/467 |
| 2018/0085096 A1* | 3/2018 | Brandl | A61B 8/469 |
| 2018/0132724 A1 | 5/2018 | Waechter-Stehle | |

* cited by examiner

HYBRID ROBOTIC-IMAGE PLANE CONTROL OF A TEE PROBE

CROSS REFERENCE TO RELATED APPLICATIONS

This application is the U.S. National Phase application under 35 U.S.C. § 371 of International Application No. PCT/EP2020/084971 filed Dec. 8, 2020, which claims the benefit of U.S. Provisional Patent Application No. 62/947, 153 filed Dec. 12, 2019. These applications are hereby incorporated by reference herein.

FIELD

The following relates generally to systems and methods of transesophageal echocardiography (TEE).

BACKGROUND

Transesophageal echocardiography (TEE) is an approach for cardiac ultrasound imaging in which the ultrasound (US) probe includes a flexible tube-like cable with the ultrasound transducer located at its distal tip. The TEE probe is inserted into the esophagus to place it close to the heart. Existing TEE probes typically include mechanical joints that, along with controlled insertion distance and angulation of the TEE probe and electronic beam steering of the ultrasound imaging plane, provide substantial flexibility in positioning the ultrasound transducer and the imaging plane so as to acquire a desired view of the heart. However, concerns include a risk of perforating the esophagus, and difficulty in manipulating the many degrees of control with unintuitive visual feedback to achieve a desired clinical view.

TEE is often used as a visualization tool for performing catheter-based cardiac interventions. In such tasks, standard views are usually obtained, so that the TEE image has a general pattern that is familiar to the operator, and thus to the interventionist controlling the catheter-based devices. As the cardiac intervention proceeds, the operator often wants to move between different standard views that provide different perspectives on the heart and catheter. Each movement of the TEE probe to a different view takes substantial time, and has the potential to cause injury to the esophagus. Moreover, the more closely the actual TEE probe position is to the standard view, the closer the US image will be to the general pattern for that view that the operator expects to see.

The following discloses certain improvements.

SUMMARY

In one disclosed aspect, an ultrasound (US) device includes: a probe including a flexible tube-like cable, ultrasonic transducers on a distal end of the tube, and mechanical joints; at least one electronic processor; and at least one memory storing computer program code. The at least one memory and the computer program code may be configured to, with the at least one electronic processor, cause the probe to steer in order to visualize a target by an iterative process in which each iteration includes: acquiring an ultrasound image using the ultrasound transducers, if the target is in a field of view (FOV) of the ultrasound image, adjusting only an electronic beam steering of the ultrasonic transducers; if the target is at an edge of the FOV of the ultrasound image, adjusting both the electronic beam steering of the ultrasonic transducers and the mechanical joints of the probe; and if the target is not in the FOV of the ultrasound image, adjusting at least the mechanical joints of the probe.

In some embodiments, the at least one electronic processor is configured to execute the computer-readable instructions to cause the US device to make the target a target view of an anatomical object based on a preset position of the distal end, and the preset position is one of: an upper esophageal position; a mid esophageal position; a transgastric position; and a deep transgastric position. In some embodiments, the at least one electronic processor is configured to execute the computer-readable instructions to cause the US device to: store at least one reference ultrasound image created by the ultrasonic transducers; and in the iteration, compare the ultrasound image with the at least one reference ultrasound image to determine if the target is in the FOV. In some embodiments, the US device further includes a database of reference images; and the at least one electronic processor may be configured to execute the computer-readable instructions to cause the US device to use the reference images to determine if the target is in the FOV.

In some implementations, the at least one electronic processor may be configured to execute the computer-readable instructions to cause the US device to: determine a motion constraint based on the ultrasound image; and in the iteration, modify the adjustment of the mechanical joints of the probe based on the determined motion constraint. In some embodiments, the US device further includes a force sensor, and the at least one electronic processor may be configured to execute the computer-readable instructions to cause the US device to: use the force sensor to determine a motion constraint; and in the iteration, modify the adjustment of the mechanical joints of the probe based on the determined motion constraint.

In some embodiments, the at least one electronic processor may be configured to execute the computer-readable instructions to cause the US device to: determine that there are multiple targets in the FOV, wherein the multiple targets include the target; and adjust the electronic beam steering to balance the multiple targets to be closer to a center of the FOV. In some embodiments, the target is a first target; and the at least one electronic processor may be configured to execute the computer-readable instructions to cause the US device to: determine that the first target and a second target are in the FOV; determine which of the first and second targets has been assigned a higher weight; and adjust the beam steering to bring the higher weight target closer to a center of the FOV. In some embodiments, the US device further includes a user interface, and the at least one electronic processor may be configured to execute the computer-readable instructions to cause the US device to: display, on the user interface, instructions how to control motion of the distal end.

In another disclosed aspect there is a method, comprising: determining that a target is in a field of view (FOV) of ultrasonic transducers; in response to the determination that the target is in the FOV, adjusting an electronic beam steering of the ultrasonic transducers; determining that the target is not in the FOV; and in response to the determination that the target is not in the FOV, adjusting mechanical joints of a probe.

In some embodiments, the method further comprises determining that the target is at an edge of the FOV; and in response to the determination that the target is at the edge of the FOV, adjusting both the electronic beam steering and mechanical joints of the probe.

In yet another disclosed aspect, there is an ultrasound (US) device, comprising: ultrasonic transducers on a distal end of a probe; at least one electronic processor; and at least one memory storing computer program code. The at least one memory and the computer program code may be configured to, with the at least one electronic processor, cause the US device to perform the following operations: (i) set a target view; (ii) determine if the target view has been reached according to a field of view (FOV) of the ultrasonic transducers; and (iii) if the target view has not been reached, either: (a) adjust a beam steering of the ultrasonic transducers, or (b) adjust mechanical joints of the probe.

In some embodiments, in the US device as described in the preceding paragraph, the at least one electronic processor may be configured to execute the computer-readable instructions to cause the US device to iterate through operations (ii)-(iii) until the target view has been reached according to the FOV.

One advantage resides in safer use of a probe, such as a transesophageal echocardiography (TEE) probe.

Another advantage resides in a TEE probe system that is easier to operate.

Another advantage resides in faster attainment of a desired TEE probe position.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Over the past approximately 15-20 years, many interventional procedures on the heart, including aortic valve repair, mitral valve repair or replacement, foramen ovale closure, and atrial septal defect closure have migrated from a surgical approach to a transcatheter approach. Transfemoral access is a common technique in which a tiny incision is made near the groin of patent to serve as an instrument portal into the femoral vein, en route to the heart. In transcatheter interventions, the clinician introduces long, flexible tools into the heart through the vasculature.

Transcatheter approaches have risen in popularity because, compared to surgery, they impose less trauma on patients and require less postoperative recovery time. At the same time, they are technically challenging procedures to perform due to lack of dexterity, visualization, and tactile feedback. Some of these capabilities are restored through technologies such as transesophageal echocardiography (TEE). In particular, TEE imaging restores visualization lost by minimal access approaches, and to a lesser extent replaces tactile feedback with visual feedback of the tool-to-tissue interactions.

Figure 1:
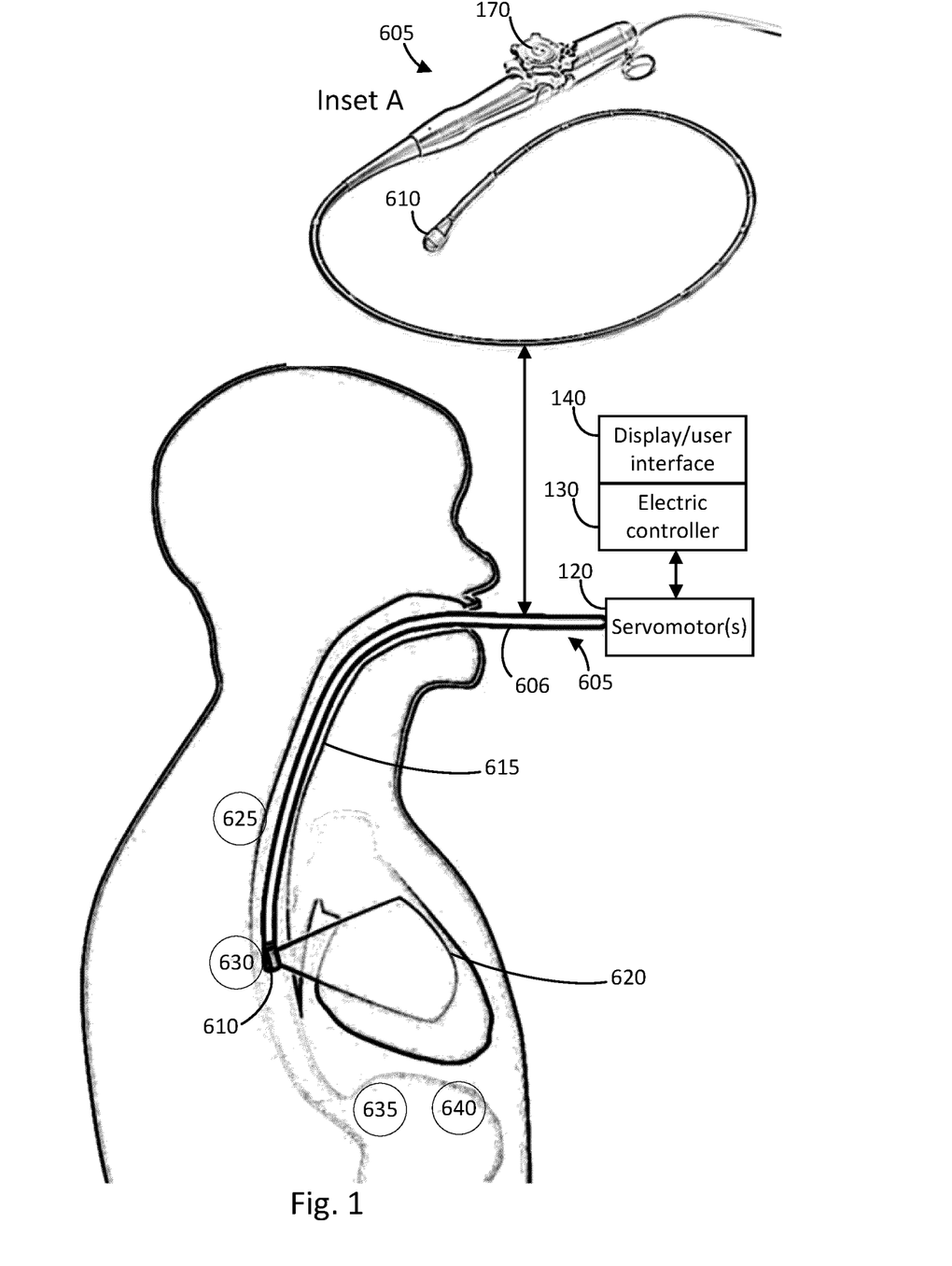
FIG. 1 illustrates an example of a probe inserted into an esophagus, and further illustrates example preset distal end positions.
Figure 3A:
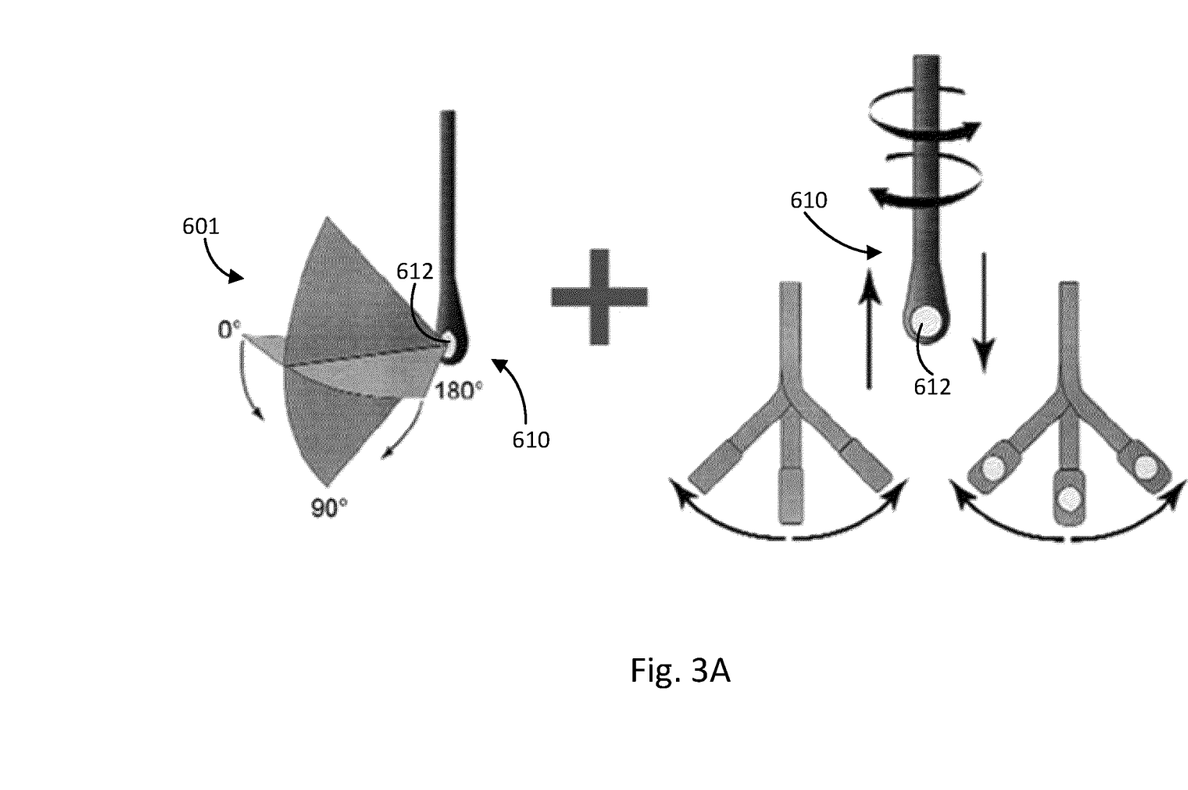
FIG. 3A shows a depiction of a basic hybrid control system that includes oversight of the 2D ultrasound imaging planes and robotic control of the TEE probe itself.
Figure 3B:
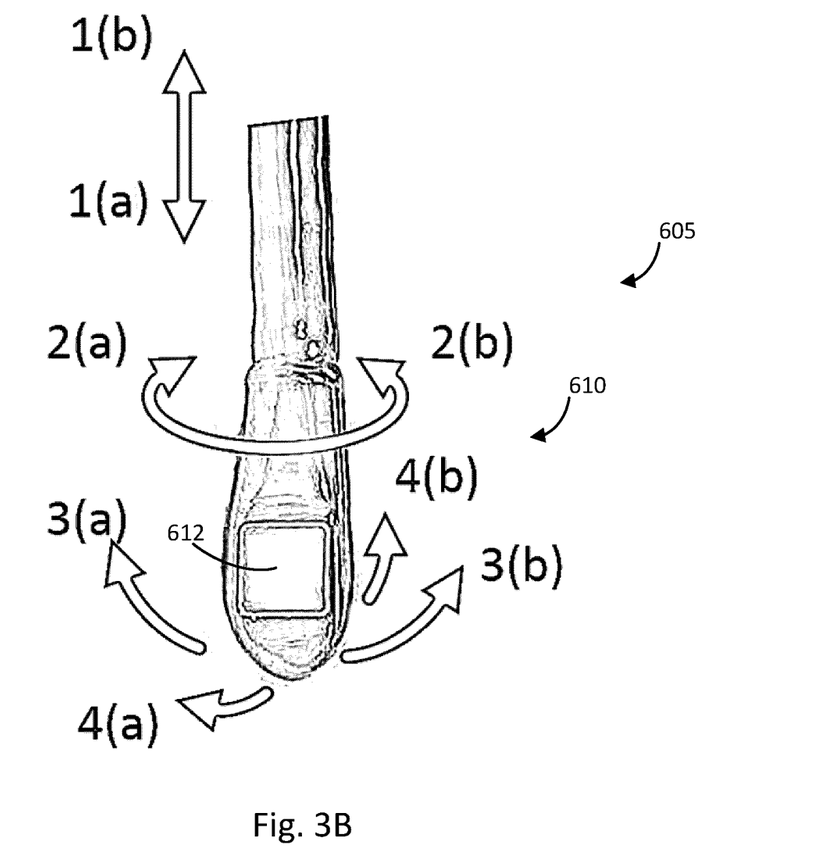
FIG. 3B illustrates degrees of freedom of the TEE probe.
Figure 3C:
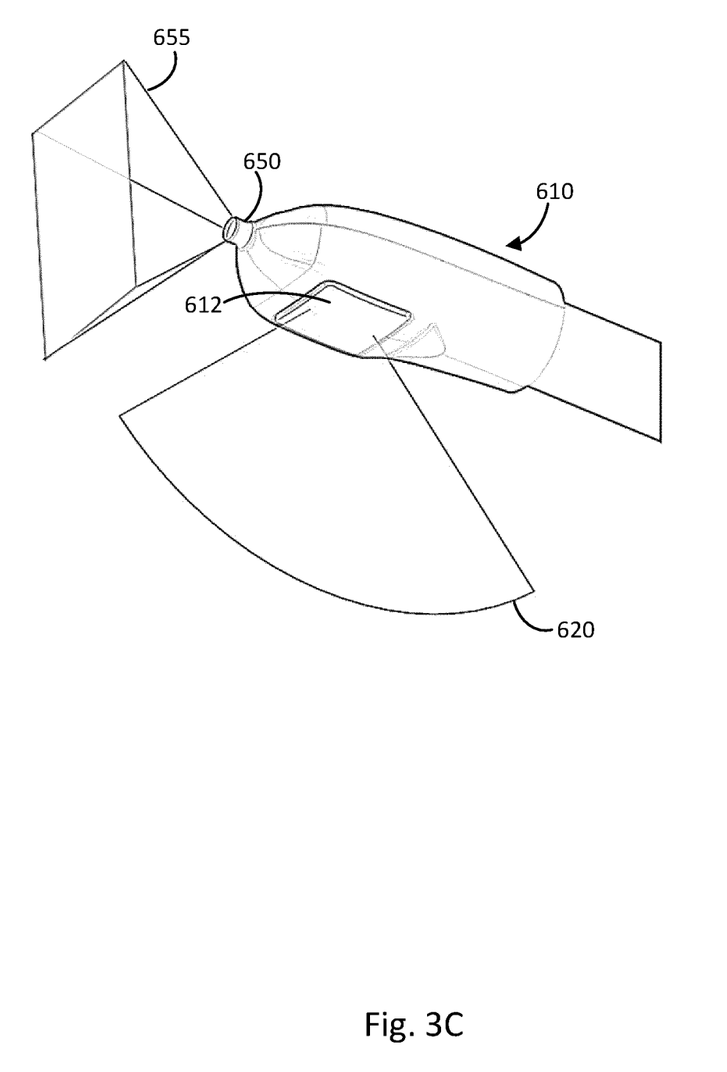
FIG. 3C illustrates an example of a distal end including both an ultrasonic FOV and a camera FOV.

Inset A of FIG. 1 illustrates probe 605 (which, in some embodiments, is TEE probe 605) including a tube 606 having a distal end 610 which includes ultrasonic transducers 612 (see FIGS. 3A, 3B, 3C; typically a phased array of side-emitting ultrasound transducers). In a manual design, the operator may control the movement of the distal end 610 by turning the knobs 170, and by manually extending (i.e. pushing) the tube 606 deeper into the esophagus, retracting (i.e. pulling) the tube 606 out of the esophagus, or rotating the tube while it is in the esophagus. Alternatively, servomotors 120 (controlled, e.g., by electric controller 130) may be used to perform these operations under computer control. A combination of manual and servomotor control is also contemplated (e.g., servomotor controlled joints and manual extension/retraction). Other types of control are also contemplated. For example, magnets, memory alloys, hydraulics, air, and so forth may also be used. The operator may use ultrasound images generated by the ultrasound transducers 612 at the distal end 610 as a guide in controlling the movement of the TEE probe.

TEE is, however, for at least the following reasons, a clumsy replacement for natural vision in critical hand-eye coordination tasks. First, ultrasound images do not offer the rich set of visual cues, including color, lighting, shading, perspective, and texture, found in natural vision and optical camera images; they are abstract representations of surgical scenarios. Second, ultrasound images can have noise and unnatural artifacts such as acoustic reflections that require cognitive effort to overcome. These first two factors combine to make ultrasound images burdensome to interpret. As a result, echocardiographers require extensive training and experience in order to become proficient. Even expert echocardiographers occasionally encounter difficult cases, as each new patient presentation is a new challenge.

Third, the vantage or viewpoint of the TEE images, originating from the esophagus behind the heart, is a different point of view than that of the clinician, forcing a disjointed hand-eye coordination that makes acquiring specific desired views difficult. Fourth, clinicians must mentally reconstruct spatial information from inside the heart from multiple cross-sectional views. In other words, one ultrasound image does not contain sufficient, actionable information. While TEE can provide 3D volumetric rendering, its visualization (e.g. resolution) often does not allow clinicians to delineate the fine details needed in practice.

Consequently, clinicians prefer higher resolution, orthogonal 2D image slices, and steer the plane angle in two dimensions (e.g., up/down, left/right). The task of adjusting both TEE probe position and image plane angle, amidst the backdrop of challenging image interpretation and disjoint hand-eye coordination, is burdensome, cognitively demanding, and ultimately susceptible to inefficiencies and errors.

The techniques described herein address these problems and others. Disclosed herein is a control system (e.g., the electronic controller 130 of FIG. 1) to robotically steer a TEE probe using servomotors 120 and automatically electronically steer image plane angles in service of finding anatomical and device views required to provide visualization in support of performing structural heart interventions, such as steering to a standard view such as standard upper esophageal (UE) view, standard mid-esophageal (ME) view, standard transgastric or deep transgastric (TG) view, or so forth. The control system can process contextual information, interpret image content, and calculate viewpoint transformations in a more efficient manner, making view acquisition a more deterministic and reliable process. In a variant embodiment in which the TEE probe is controlled by manual knobs 170 and manual tube extension/retraction rather than servomotors 120, the control system may provide human-perceptible directions (e.g., "retract probe", "advance probe", "turn probe to the right", et cetera), displayed on a control computer display (such as the display 140 of FIG. 1, and/or articulated using a speech synthesizer) for assisting in manual control of the TEE probe. The electronic controller 130 suitably comprises at least one electronic processor that reads and executes instructions (i.e. computer program code) stored in at least one memory (i.e. at least one non-transitory storage medium) in order to perform the disclosed TEE probe control methods. The electronic processor may, for example, comprise a computer having one or more digital or analog ports for operatively communicating with the servomotor(s) 120. For example, the communication can be digital communication via a USB port or other standard digital port, or may be via digital and/or analog control signals generated by a dedicated control I/O card installed in the computer, and/or so forth. In some embodiments, the electronic controller 130 may be integral with the ultrasound imaging controller that controls the ultrasound imaging performed by the TEE probe 605, in which case the display 140 also presents ultrasound images acquired by the TEE probe 605.

Figure 2:
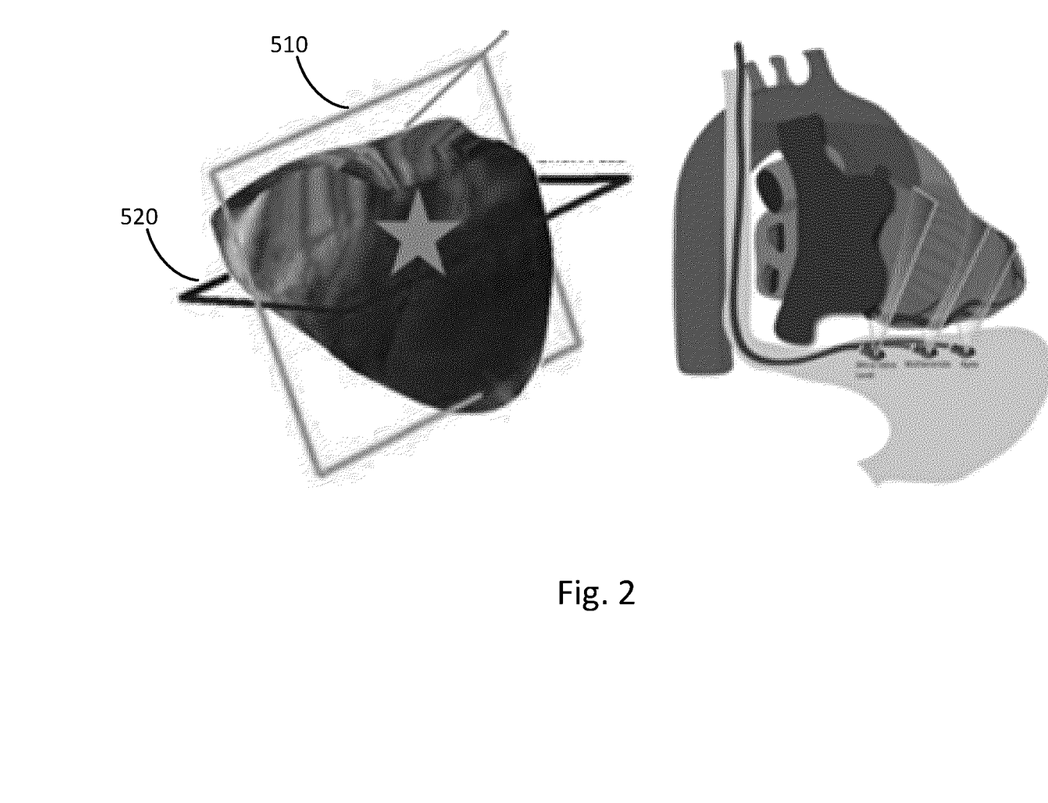
FIG. 2 illustrates TEE views for a transseptal puncture procedure.

By way of a non-limiting example, FIG. 2 illustrates TEE views for providing visualization during a transseptal puncture procedure. Long axis 510 and short axis 520 outline orthogonal image planes containing the needle and the target puncture site in the septum. These views may be difficult to find by manipulation of the TEE probe, and furthermore clinicians may need to move the probe to a different view and then attempt to restore these views afterwards.

The many degrees of freedom are cognitively difficult to manage efficiently, especially given image/spatial interpretation challenges. With reference to FIG. 3A, the ultrasonic transducers 612 are typically a phased array of ultrasound transducers that generate an electronically steerable image plane 601, where FIG. 3A, left hand drawing, shows an example of electronic beam steering. FIG. 3A, right hand drawings, show additional degrees of freedom attainable by controlling joints of the TEE probe 605 using the servomotors 120 or (in the variant manual embodiment) knobs 170. The architecture of the joint control mechanisms can vary, for example as a non-limiting example employing control wires connected to the joints and passing through the lumen of the tube 606 to connect with the servomotors 120 or knobs 170.

FIG. 3B further illustrates degrees of freedom of the distal end 610 (which includes ultrasonic transducers) of the probe 605. For example, the distal end 610 may be moved: along an axial direction of the probe, as in directions 1(a) and 1(b); in circular directions, as in directions 2(a) and 2(b); or in pivotal directions, as in directions 3(a), 3(b), 4(a) and 4(b). In some embodiments, the movement in the directions 1(a), 1(b), 2(a), 2(b), 3(a), 3(b), 4(a) and 4(b) is accomplished by mechanical joints. In some implementations, the mechanical joints include servomotor-driven extension/retraction of the tube 606. It should be noted that FIGS. 3A and 3B show an illustrative example, and that more or fewer, and/or different, degrees of freedom may be provided in a specific TEE probe design.

Figure 3D:
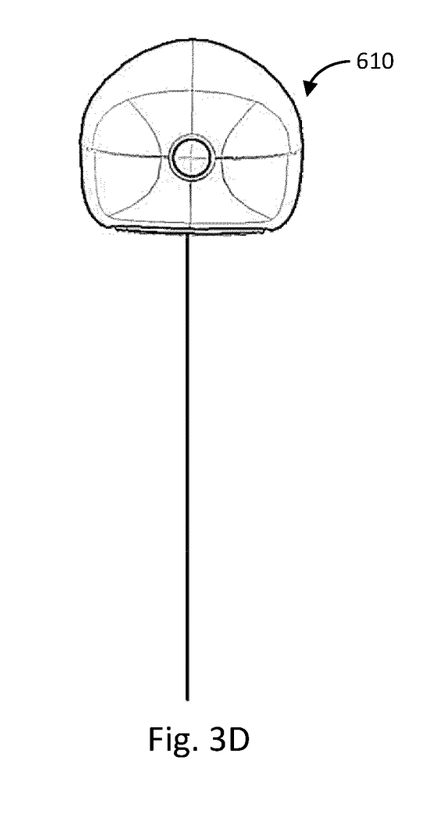
FIG. 3D illustrates a front view of an example distal end.
Figure 3E:
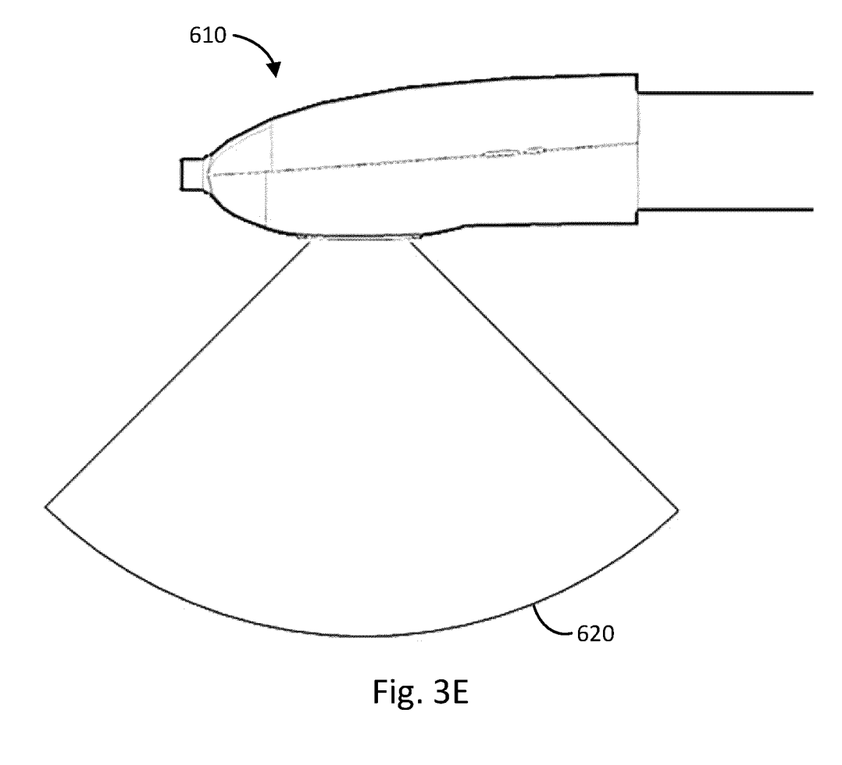
FIG. 3E illustrates a side view of an example distal end.

FIGS. 3C, 3D, and 3E illustrate an embodiment where the distal end 610 further includes camera sensor 650 which has camera FOV 655. In this variant embodiment, the side-emitting ultrasonic transducers 612 are augmented by the forward viewing optical camera 650. (In another variant embodiment, the camera sensor 650 may be a second, forward-emitting ultrasonic transducer array). It should be understood that, throughout this disclosure, unless specified otherwise, the term "FOV" can refer to either the ultrasonic FOV or the camera FOV. FIG. 3D illustrates a front view of an example distal end. FIG. 3E illustrates a side view of an example distal end.

FIG. 1 illustrates an example of the probe 605 inserted into an esophagus 615, and illustrates an example ultrasonic FOV 620. For 2D ultrasound imaging, the FOV 620 is typically a two-dimensional wedge. FIG. 1 further illustrates example preset distal end positions, which may correspond to standard TEE views such as: upper esophageal position 625; mid esophageal position 630; transgastric position 635; and deep transgastric position 640.

Generally, in some embodiments, there is a control system to robotically steer the probe and/or distal end, and automatically steer the image plane angles in service of finding the anatomical and device views required to provide visualization for performing structural heart interventions. The control system can digest contextual information, interpret image content, and calculate viewpoint transformations in an efficient manner, making view acquisition a more deterministic and reliable process compared with unassisted manual manipulation of the TEE probe.

Put another way, some embodiments involve an improvement in which the manual control of the TEE probe 605 is augmented or replaced by robotic control. Some implementations use a set of rules for iterative robotic control, including, for each iteration: adjusting only the electronic beam steering if the target is in the field of view (FOV); adjusting both the beam steering and the mechanical joints if the target is at the edge of the FOV, biasing toward electronic beam steering; and adjusting only the mechanical joints if the target is not in the FOV. To recognize the target, a database of reference ultrasound images at standard views may be used, or a model of the standard ultrasound view may be used (e.g., a view in which all four chambers of the heart are visible can be modeled using the expected four-compartment image format). In another approach, if the clinician is at a particular view then this image may be stored as a reference image, and if the clinician later wishes to return to that view then the stored reference image is retrieved.

In addition, some embodiments use Intracardiac Echo (ICE) probes (rather than the above-described TEE probes) which are thin probes that are inserted into the heart. The approaches described herein are able to properly position these probes with respect to the Right Atrium, Left Atrium, etc. In other embodiments, Intravascular Ultrasound (IVUS) probes are used, which are thin probes used in blood vessels. In addition, some implementations include endobronchial US, and some implementations include transrectal US and transurethral US for urology. It should be understood that the techniques described herein include any in-body ultrasound imaging in general.

Figure 4:
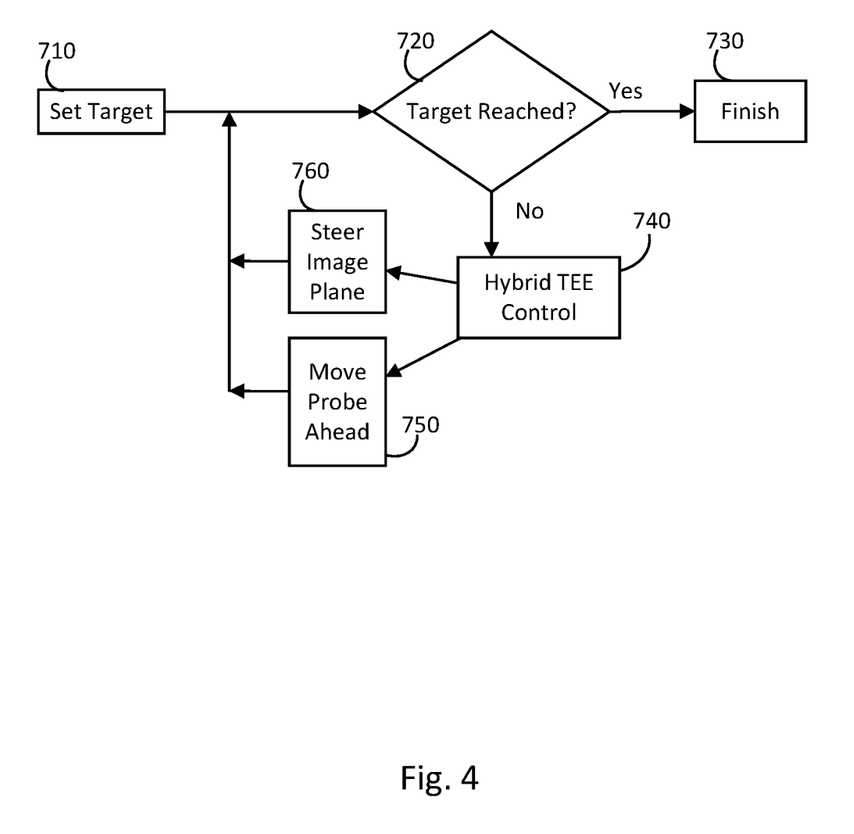
FIG. 4 diagrammatically illustrates an example embodiment of a hybrid control strategy to coordinate motion of both robotic TEE probe and the image planes angles.

In one embodiment, the hybrid TEE probe-image plane controller follows the strategy depicted in the example of FIG. 4. The controller is triggered by setting a desired target view at operation 710, which may be specified either directly as a set of robotic joint positions and plane angles, or visually as the desired target images then internally converted to corresponding joints and angles. For example, if a particular view is stored as a reference image together with the set of robotic joint positions and plane angles, and if the clinician later wishes to return to that view, then the stored reference image is converted to corresponding joints and angles by retrieving the stored corresponding joints and angles. In some embodiments, the operator may set the target position to be one of the preset target positions illustrated in FIG. 1 (upper esophageal position 625; mid esophageal position 630; transgastric position 635; and deep transgastric position 640). For example, the expected joint and angle positions may be tabulated for the standard views in a data structure (e.g. table) supplied with the TEE probe. Preferably, the expected joints and angles are tabulated for different patient-specific parameters such as patient size. If the target has been reached, at operation 720, the procedure finishes at operation 730. If the target has not been reached, the hybrid TEE controller performs functions at operation 740. Specifically, the robot joints and image plane angles must then move from its initial configuration to converge towards the target view. The hybrid TEE controller may budge both the probe (operation 750) and image planes (operation 760) in the necessary directions and repeatedly checks whether the target view has been reached (operation 720). During each iterative check 720, the controller decides how to set the next motion increment based on a variety of factors. This process repeats until the target views are reached. If the views are not attainable, the controller halts and indicates an error and if possible, provides a suggestion for resetting the probe position to a known state.

In performing the operation 740, comparison of the currently acquired ultrasound image with the reference ultrasound image at standard view (or, alternatively, with a model of the standard ultrasound view) is preferably performed. This is because, although the target is specified at operation 710 in terms of joints and angles as previously discussed, in practice it is expected that those joint and imaging plane angle positions may not provide precisely the desired ultrasound imaging view. For example, in the case of using a table of expected joint and angle positions supplied with the TEE probe, the specific patient's anatomy is likely to be sufficiently different so that simply setting the table joint and angle positions will not provide exactly the correct view. When using joint and angle positions stored with a stored previous image as the target, hysteresis and/or TEE probe drift or so forth, may again result in not achieving precisely the same view when returning to the stored joint and angle positions.

To address this, the controller employs image-based adjustment as the target is approached. Hence, after each iteration, an ultrasound image is acquired and it is determined (based on comparison of the currently acquired ultrasound image with the reference ultrasound image or model of the standard ultrasound view) whether the target is in the FOV of the ultrasound image. If not (as will likely be the case in at least the initial iterations), then the hybrid TEE controller moves the probe only, in the direction moving toward the joint and angle positions specified for the target. Hence, after each iteration the ultrasound image is compared with the reference ultrasound image at standard view (or, alternatively, with the model of the standard ultrasound view). As long as the target is not in the ultrasound FOV, the iterations perform only operation 750, i.e. moving the probe without adjusting the beam angle. When the target comes barely into the FOV, the hybrid TEE controller may both: (i) move the probe and/or distal end of the probe per operation 750, and also (ii) steer the image plane per operation 760. After one or more iterations of this hybrid position/plane angle adjustment, the target will likely be closer to being centered in the FOV. At this point, only the beam angle is adjusted (operation 760).

To summarize, regarding the hybrid TEE controller in the example of FIG. 4, in operation 740, the hybrid TEE controller may consider if the target is in the field of view (FOV). If so, the hybrid TEE controller may steer the image plane first (e.g. by beam steering ultrasonic transducers of the distal end of the probe). If not, the hybrid TEE controller may move the probe or distal end of the probe. If the target is barely in the FOV, the hybrid TEE controller may both: (i) move the probe and/or distal end of the probe, and (ii) steer the image plane. Further, in operation 740, the hybrid TEE controller may consider if the plane angle is reachable, and if there are motion constraints (e.g. as determined by a force sensor, as will be explained in more detail below).

Not all embodiments are fully automatic. For example, in some embodiments, the angles of the image plane and/or distal end position may be computed and presented to the user as recommendation(s), to be then implemented by the user via the knobs 170 and/or by extending or retracting the tube 606.

The following will describe example criteria to calculate next motion increment. Clinicians prefer to set views such that the imaging targets of interest, such as an anatomical feature, interventional instrument, or some combination thereof are approximately centered within the 3D ultrasonic image, and in some cases from a particular viewpoint. This arrangement makes the views robust to minor displacements of the TEE probe due to inadvertent probe motion, patient motion, or physiological motion. If imaging targets instead reside at the edge of the volume, they may easily leave the view thereby causing clinicians to lose desired visualization. Therefore, one criteria to decide on the next motion increment is whether the imaging target is near the center of the field of view (e.g. for a discrete target, by determining if a center or edge of the target is a predetermined length from the center of the FOV; for a target viewpoint, the motion criteria may be the similarity between the current viewpoint and the desired viewpoint, which may be computed by registering the two views to determine the distance between them and making, for example, 0 distance be a match). If so, the probe head is kept still while the imaging planes are adjusted (e.g. by beam steering ultrasonic transducers of the distal end of the probe). Otherwise, the distal end is moved so that the imaging targets can be as close as possible to the center of the FOV. This strategy embeds a preference to minimize probe motion, as the available range of motion inside the esophagus is limited. When both the probe and image planes must be moved in an iteration, they can be moved one after the other or simultaneously.

It should further be noted that 'centering' is an example of a desired view of a target. For instance, sometimes a target is preferred at some offset from the center of the image, but the concepts and procedures are the same as described above.

There may be situations in which the imaging target cannot be centered in the ultrasound volume exactly due to physical limitations of the probe, in which case the target is centered as much as possible and plane angle steering is favored. Physical limitations may include intrinsic constraints such as joint limits, extrinsic constraints such as those imposed by the anatomy, or a combination of the two.

These anatomical limitations can be: (i) sensed by a separate force sensor (ii) inferred from tissue compression observed in ultrasound images, and/or (iii) measured through strain images. In other words, optionally, the TEE probe can incorporate a force sensor or sensors to detect when the probe is impinging upon the inner surface of the esophagus. Other disclosed approaches detect such an impingement event from tissue compression observed in the ultrasound images, or measured through strain images. Advantageously, these constraints make use of the TEE probe much safer.

If there are multiple imaging targets present in the desired views, the system may balance the constellation of targets to be centered in the volume (e.g. by beam steering). Alternatively, the targets may be weighted such that those with higher weights are shown more towards the center of the imaging volume than those with lower weights.

Some embodiments assume the plane angles correspond to orthogonal X-planes. Other embodiments are applicable to planes at arbitrary angles as well.

Some embodiments use a similarity metric between desired views and attainable views. Specifically, in practice, views can be difficult to replicate precisely due to changing anatomical conditions and imperfect robot kinematics. To handle these conditions, image-based matching between current views and desired views can be used to calculate a similarity metric, and the controller can halt once the similarity reaches a threshold. Alternatively, a similarity metric can use probe configuration, and/or plane angles as an input; or, in yet other embodiments, the probe position can be tracked extrinsically with respect to the anatomy, and the similarity between attainable views and desired target views can be measured accordingly.

Some embodiments use data driven control. Specifically, as an alternative to analytical, explicit control over the probe and planes, these parameters can be determined empirically based on a database of stored views.

Some embodiments also involve a user interface. Specifically, the application of this invention can be used to direct the user to perform the motions explicitly or the system can execute required actions automatically. Semi-automation of view finding is applicable as well.

Some embodiments use an intra-procedural update of views. Specifically, to handle the problem of changing anatomical or interventional conditions, which prevent precise replication of views, desired views can be updated using the closest attainable views.

It will be further appreciated that the techniques disclosed herein may be embodied by a non-transitory storage medium (i.e. at least one memory) storing instructions readable and executable by an electronic data processing device (e.g., the controller 130 of FIG. 1) to perform the disclosed techniques. Such a non-transitory storage medium may comprise a hard drive or other magnetic storage medium, an optical disk or other optical storage medium, a cloud-based storage medium such as a RAID disk array, flash memory or other non-volatile electronic storage medium, or so forth.

The invention has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof

The invention claimed is:

1. An ultrasound (US) device, comprising:
 a probe including a tube and ultrasonic transducers on a distal end of the tube, the tube including mechanical joints, the ultrasound transducers configured to generate an electronically steerable image plane defining a two-dimensional field of view (2D FOV) of an ultrasound image, and the mechanical joints configured to physically position the ultrasound transducers;
 at least one electronic processor; and
 at least one memory storing computer program code;
 the at least one memory and the computer program code configured to, with the at least one electronic processor, cause the probe to steer to a target by an iterative process in which each iteration includes:
  acquiring the ultrasound image using the ultrasound transducers; and
  at least one of: (i) electronically steering the image plane of the ultrasonic transducers to electronically adjust the 2D FOV according to the ultrasound image, and (ii) adjusting the mechanical joints of the probe to physically reposition the ultrasound transducers according to the ultrasound image.

2. The US device of claim 1, wherein the at least one electronic processor is configured to execute the computer-readable instructions to cause the US device to, in each iteration:
 if the target is in the 2D FOV of the ultrasound image, only electronically steering the image plane of the ultrasonic transducers;
 if the target is at an edge of the 2D FOV of the ultrasound image, both electronically steering the image plane of the ultrasonic transducers and adjusting the mechanical joints of the probe; and
 if the target is not in the 2D FOV of the ultrasound image, at least adjusting the mechanical joints of the probe.

3. The US device of claim 1, wherein the at least one electronic processor is configured to execute the computer-readable instructions to cause the US device to make the target a target view of an anatomical object based on a preset position of the distal end, and wherein the preset position is one of:
 an upper esophageal position;
 a mid esophageal position;
 a transgastric position; and
 a deep transgastric position.

4. The US device of claim 1, wherein the at least one electronic processor is configured to execute the computer-readable instructions to cause the US device to:
 store at least one reference ultrasound image created by the ultrasonic transducers; and
 in the iteration, compare the ultrasound image with the at least one reference ultrasound image to determine if the target is in the 2D FOV.

5. The US device of claim 1, further comprising a database of reference images;
 wherein the at least one electronic processor is configured to execute the computer-readable instructions to cause the US device to use the reference images to determine if the target is in the 2D FOV.

6. The US device of claim 1, wherein the at least one electronic processor is configured to execute the computer-readable instructions to cause the US device to:
 determine a motion constraint based on the ultrasound image; and
 in the iteration, modify the adjustment of the mechanical joints of the probe based on the determined motion constraint.

7. The US device of claim 1, further comprising a force sensor, and wherein the at least one electronic processor is configured to execute the computer-readable instructions to cause the US device to:
use the force sensor to determine a motion constraint; and
in the iteration, modify the adjustment of the mechanical joints of the probe based on the determined motion constraint.

8. The US device of claim 1, wherein the at least one electronic processor is configured to execute the computer-readable instructions to cause the US device to:
determine that there are multiple targets in the 2D FOV, wherein the multiple targets include the target; and
electronically steer the image plane of the ultrasound transducers to balance the multiple targets to be closer to a center of the 2D FOV.

9. The US device of claim 1, wherein:
the target is a first target; and
the at least one electronic processor is configured to execute the computer-readable instructions to cause the US device to:
determine that the first target and a second target are in the 2D FOV;
determine which of the first and second targets has been assigned a higher weight; and
adjust the beam steering to bring the higher weight target closer to a center of the 2D FOV.

10. The US device of claim 1, further comprising a user interface, wherein the at least one electronic processor is configured to execute the computer-readable instructions to cause the US device to:
display, on the user interface, instructions for how to control motion of the distal end.

11. The US device of claim 1, wherein the at least one memory and the computer program code is configured to, with the at least one electronic processor, in the iteration, cause the probe to steer to a target by:
if the target is not in the 2D FOV of the ultrasound image, adjusting only at least the mechanical joints of the probe.

12. A method, comprising:
acquiring an ultrasound image using ultrasound transducers, the ultrasound transducers configured to generate an electronically steerable image plane defining a two-dimensional field of view (2D FOV);
determining whether a target is in the 2D FOV of the ultrasonic transducers;
upon a determination that the target is in the 2D FOV, electronically steering the image plane of the ultrasonic transducers to electronically reposition the 2D FOV; and
upon a determination that the target is not in the 2D FOV, adjusting mechanical joints of a probe to physically reposition the ultrasonic transducers.

13. The method of claim 12, further comprising:
upon a determination that the target is at the edge of the 2D FOV, both the electronically steering the image plane and adjusting the mechanical joints of the probe.

14. An ultrasound (US) device, comprising:
ultrasonic transducers on a distal end of a probe, the ultrasound transducers configured to generate an electronically steerable image plane defining a two-dimensional field of view (2D FOV), and the probe including mechanical joints configured to physically position the ultrasound transducers;
at least one electronic processor; and
at least one memory storing computer program code;
the at least one memory and the computer program code configured to, with the at least one electronic processor, cause the US device to perform the following operations:
(i) set a target view;
(ii) determine if the target view has been reached according to the 2D FOV of the ultrasonic transducers; and
(iii) if the target view has not been reached, either: (a) electronically steer the image plane of the ultrasonic transducers, or (b) adjust the mechanical joints of the probe.

15. The US device of claim 14, wherein the at least one electronic processor is configured to execute the computer-readable instructions to cause the US device to iterate through operations (ii)-(iii) until the target view has been reached according to the 2D FOV.

16. The US device of claim 14, wherein the at least one electronic processor is configured to execute the computer-readable instructions to cause the US device to make the target a target view of an anatomical object based on a preset position of the distal end, and wherein the preset position is one of:
an upper esophageal position;
a mid esophageal position;
a transgastric position; and
a deep transgastric position.

17. The US device of claim 14, wherein the at least one electronic processor is configured to execute the computer-readable instructions to cause the US device to:
determine a motion constraint based on the ultrasound image; and
modify the adjustment of the mechanical joints of the probe based on the determined motion constraint.

18. The US device of claim 14, further comprising a force sensor, and
wherein the at least one electronic processor is configured to execute the computer-readable instructions to cause the US device to:
use the force sensor to determine a motion constraint; and
modify the adjustment of the mechanical joints of the probe based on the determined motion constraint.

19. The US device of claim 14, wherein the at least one electronic processor is configured to execute the computer-readable instructions to cause the US device to:
determine that there are multiple targets in the 2D FOV, wherein the multiple targets include the target; and
adjust the electronic beam steering to balance the multiple targets to be closer to a center of the 2D FOV.

20. The US device of claim 1, wherein at least one iteration of the iterative process includes both electronically steering the image plane of the ultrasound transducers and adjusting the mechanical joints of the probe.

* * * * *